(12) United States Patent
Gauthier

(10) Patent No.: US 8,377,070 B2
(45) Date of Patent: Feb. 19, 2013

(54) COMPRESSOR DISTRACTOR TOOL

(76) Inventor: Michael T. Gauthier, Grafton, WI (US)

( * ) Notice: Subject to any disclaimer, the term of this patent is extended or adjusted under 35 U.S.C. 154(b) by 1311 days.

(21) Appl. No.: 12/123,006

(22) Filed: May 19, 2008

(65) Prior Publication Data
US 2008/0287995 A1 Nov. 20, 2008

Related U.S. Application Data

(60) Provisional application No. 60/938,638, filed on May 17, 2007.

(51) Int. Cl.
*A61B 17/60* (2006.01)
(52) U.S. Cl. .......................................................... 606/90
(58) Field of Classification Search .................... 606/90
See application file for complete search history.

(56) References Cited

U.S. PATENT DOCUMENTS

| | | | |
|---|---|---|---|
| 5,059,194 A | 10/1991 | Michelson | |
| 6,261,296 B1 | 7/2001 | Aebi et al. | |
| 6,712,825 B2 | 3/2004 | Aebi et al. | |
| 6,761,723 B2 | 7/2004 | Buttermann et al. | |
| 2005/0059976 A1* | 3/2005 | Bryan et al. | 606/80 |
| 2008/0262318 A1* | 10/2008 | Gorek et al. | 600/235 |

* cited by examiner

*Primary Examiner* — Bruce E Snow

(57) ABSTRACT

A combined compressor and distractor tool is provided that includes a mechanism capable of switching the mode of operation of the tool from a compression tool to a distraction tool. The tool includes engagement tips and handles at opposed ends of the tool that are pivotally connected to a central shaft. A saddle is slidably mounted on the shaft between and pivotally connected to the handles. When the saddle is engaged with the shaft in a before center position, squeezing the handles results the movement of the shaft forwardly to operate the engagement tips as a distractor. However, when the saddle is engaged with the shaft in a past, or over center position, squeezing the handles results the movement of the shaft rearwardly to operate the engagement tips as a compressor.

4 Claims, 3 Drawing Sheets

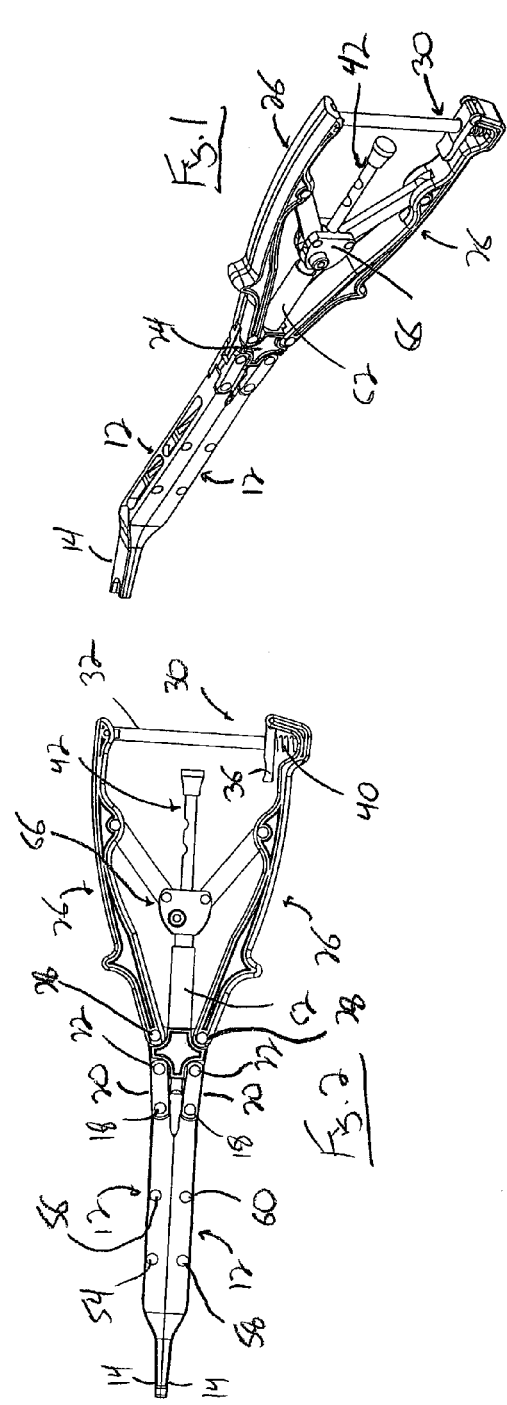

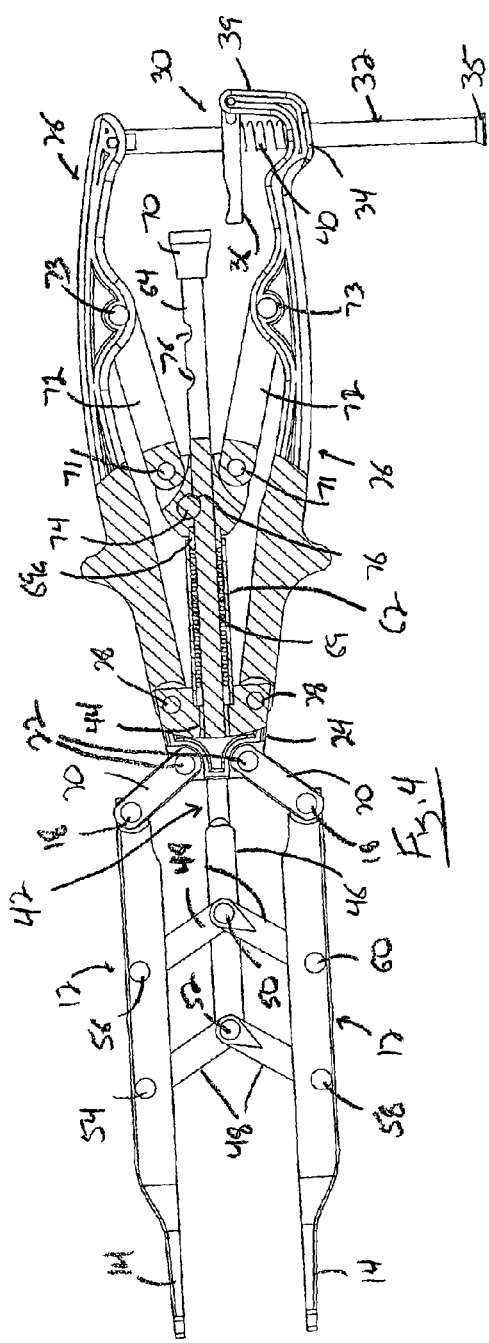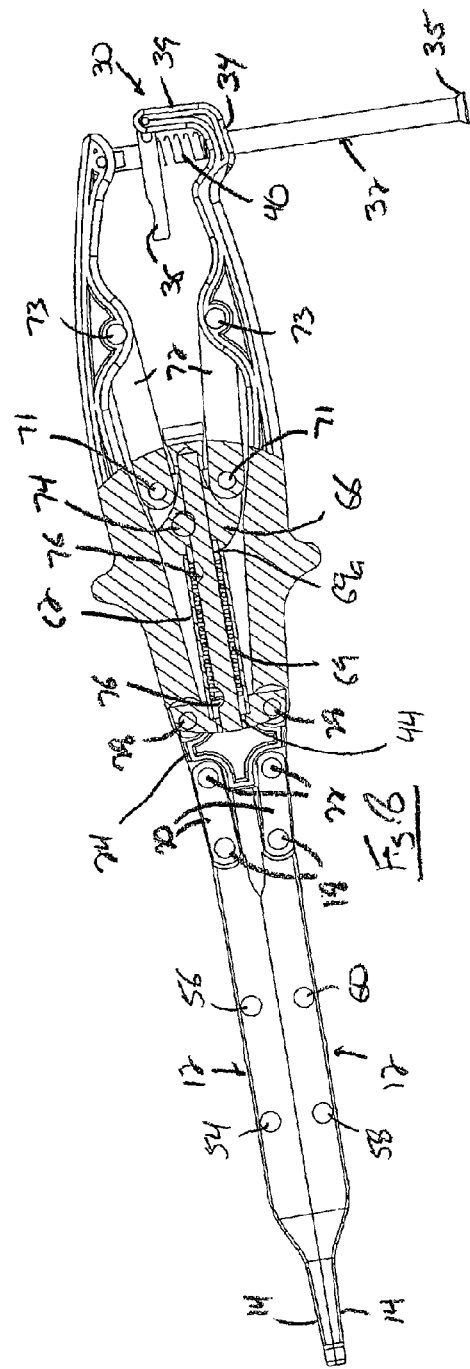

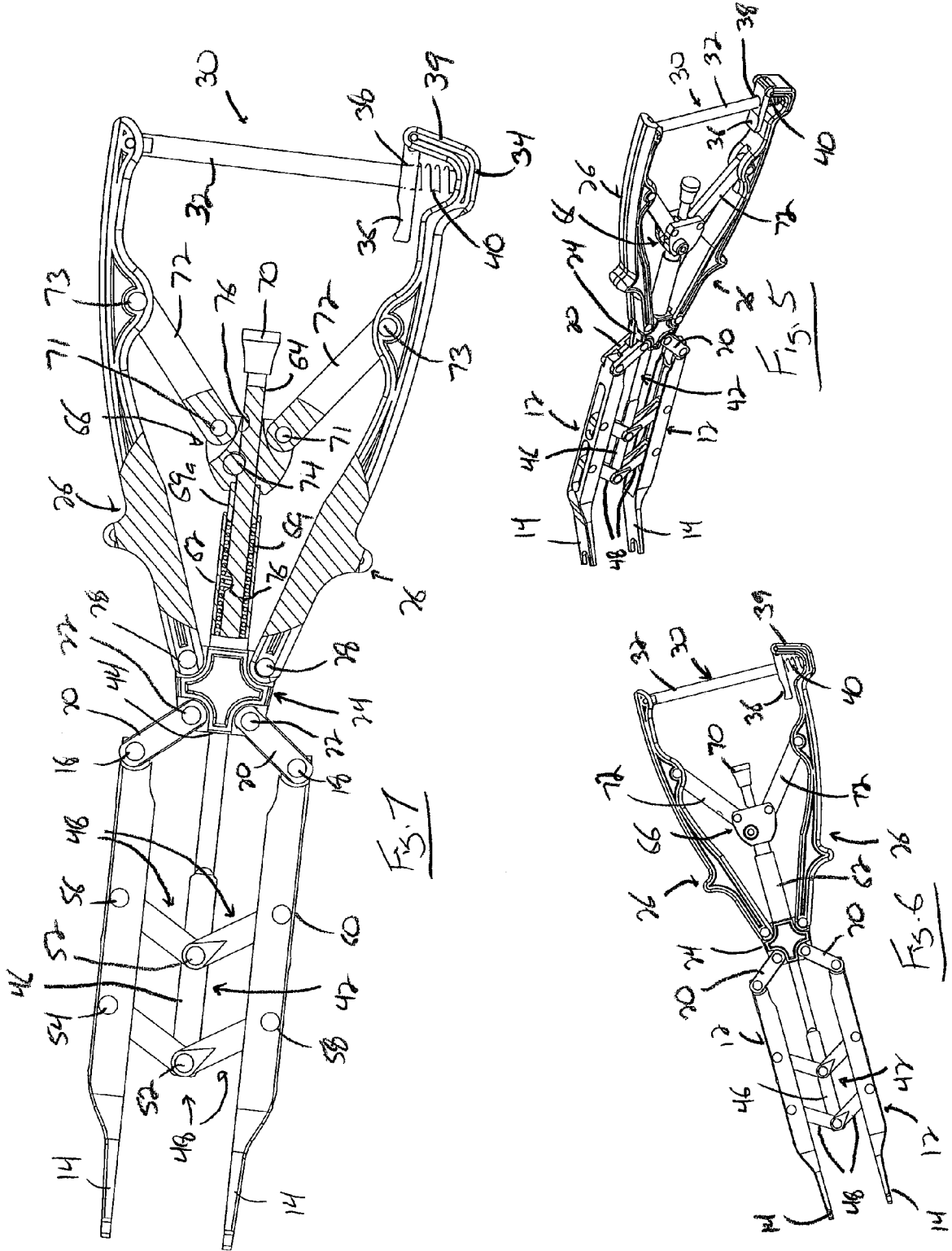

COMPRESSOR DISTRACTOR TOOL

CROSS-REFERENCE TO RELATED APPLICATIONS

This application claims priority from Provisional U.S. Patent Application Ser. No. 60/938,638, filed on May 17, 2007 and incorporated herein in its entirety.

FIELD OF THE INVENTION

The present invention relates to a spinal compressor instruments and spinal distractor instruments and more particularly to an instrument combining the compression and distraction functions.

BACKGROUND OF THE INVENTION

In order to perform a surgical procedure in which the separation of various physical components, such as spinal vertebrae, is required, a tool called a distractor is necessary for displacing the physical components from one another. The distractor operates by mechanically converting a compressive force exerted by an individual on a handle located at one end of the distractor into an opposite expanding movement for a pair of engagement tips of the distractor disposed opposite the handle. To accomplish this, the distractor is formed with a number of mechanical linkages that extend between the handles and the distractor tips. These linkages are pivotally connected to one another in a manner that converts the inward movement of the handles into outward movement of the distractor tips.

In other situations or surgical procedures it is necessary to compress physical components towards one another. In these procedures, it is necessary to employ a tool called a compressor that operates by mechanically converting a compressive force exerted by an individual on a handle located at one end of the compressor into a corresponding compressive force for a pair of engagement tips on the compressor disposed opposite the handle. To perform this function, the compressor is most often formed with a simple scissors linkage such that an inward and compressive force on the handle is translated into an inward compressive force on the compressor tips.

However, in many surgical procedures both a compressor and a distractor are necessary for proper completion of the procedure, and often times are utilized in the same location in which the procedure is performed. Because the compressor and the distractor are formed as separate tools, it is necessary to have both a compressor and a distractor available such that each tool can be utilized when required during the surgical procedure. For this reason, many kits for use in spinal procedures include both a compressor and a distractor in them. However, the requirement for having compressor and distractor tools present during a procedure can create problems with regard to a number of tools present during a surgical procedure, especially when one of the tools becomes contaminated, i.e., is dropped, and needs to be sterilized.

As a result, it is desirable to develop a tool that can function as both a compressor and a distractor depending upon the particular situation in the surgical procedure being performed.

SUMMARY OF THE INVENTION

According to one aspect of the present invention, a tool is provided that can function as either a compressor or a distractor depending upon the operative configuration of the tool. The tool is formed with a pair of engagement tips pivotally connected to a central member such that the tips can be moved laterally towards and away from one another due to the pivoting movement of the pivot arms with regard to the central member. Opposite the tips, the tool includes a pair of handles also pivotally connected directly to the central member for movement with respect to the central member. A central shaft is slidably disposed within and extends through a channel formed in the central member, such that opposite ends of the shaft are positioned between the tips and the handles. Between the tips, the shaft includes pairs of pivoting members connected to the shaft at one end and to the tips at the opposite end of each pivoting member. Between the handles, the shaft includes a saddle slidably mounted to the shaft and pivotally connected to the handles at locations spaced from the central member by additional pivot members. The saddle can be selectively engaged with the shaft at various locations on the shaft to position the saddle in either a before center or an over center location on the shaft. By moving the saddle between these locations, the tool is capable of mechanically translating the compressive force exerted on the handles into either a compressive or distraction force on the tips.

According to another aspect of the present invention, the handles are connected to one another opposite the central member by an adjustable locking rod. The rod includes a spring-biased locking member that can be engaged with slide extending between the handles when the handles are positioned at any configuration along the slide with respect to one another.

Numerous other aspects, features, and advantages of the present invention will be made apparent from the following detailed description together with the drawings figures.

BRIEF DESCRIPTION OF THE DRAWINGS

The drawings illustrate the best mode currently contemplated of practicing the present invention.

In the drawings:

FIG. 1 is an isometric view of a convertible compressor/distractor tool constructed according to the present invention in a distraction configuration FIG. 2 is a side plan view of the tool of FIG. 1;

FIG. 3 is a partially broken away side plan view of the tool of FIG. 1;

FIG. 4 is a partially broken away side plan view of the tool of FIG. 1 in an engaged position;

FIG. 5 is an isometric view of the tool of FIG. 1 in a compression configuration;

FIG. 6 is a side plan view of the tool of FIG. 5;

FIG. 7 is a partially broken away side plan view of the tool of FIG. 5; and FIG. 8 is a partially broken away side plan view of the tool of FIG. 5 in an engaged position.

DETAILED DESCRIPTION OF THE INVENTION

With reference now to the drawing figures in which like reference numerals designate like parts throughout the disclosure, a convertible compressor/distractor tool constructed according to the present invention is indicated generally at 10 in FIGS. 1 and 2. The tool 10 includes a pair of tip members 12 at one end, each including a tip 14 and a body 16 extending from the tip 14. The tips 14 can be integrally formed with the body 16 of each tip member 12, or can be releasably secured thereto utilizing any suitable mechanism. The tips 14 can additionally be formed from materials different from that used in forming the body 16, which normally is a metal, such as stainless steel, such that the tips 14 can be formed from plastics, such as transparent plastics that enable an individual to view objects through the tips 14 when the tool 10 is in use. Further, the releasable attachment of the tips 14 to the body 16 of the tip members 12 allows the tips 14 to be removed and replaced should they become damaged.

Alternatively, the tool 10 can include only a single movable tip member 12, with the tip member 12 movable with respect to a stationary member (not shown) to provide the compression or distraction function.

Referring now to FIGS. 4-7, the tip members 12 are each pivotally connected by a pivot pin 18 to one end of a pair of the first pivot arms 20. Opposite the tip members 12, the pair of first pivot arms 20 are each pivotally connected by pivot pins 22 to a supporting central member 24. However, in addition to pins 22, the first pivot arms 20 can also be pivotally connected to the tip members 12 with other structures, such as members (not shown) that may slide and rotate within respect to the engagement tips 12 in order to allow the tip members 12 move and provide the different functionalities of the tool 10.

Opposite the tip members 12, a pair of gripping handles 26 are each movably, and preferably pivotally connected to the central member 24 by pivot pins 28 or other suitable connectors. Alternatively, similar to the tip members 12, the tool 10 can include only a single movable handle 26, with the handle 26 movable with respect to a stationary member (not shown) to provide the compression or distraction function.

The handles 26 are each formed of a generally rigid material, such as a metal, and preferably are formed with a shape that is conducive to easy gripping of the handles 26 by an individual. Opposite the central member 24, the gripping handles 26 are connected to one another by a locking mechanism 30. The locking mechanism 30 includes a slide or rod 32 connected, preferably pivotally, at one end to one of the gripping handles 26, and slidably received within a bore 34 disposed in the opposite handle 26. The rod 32 includes a stop surface 35 opposite the end of the rod 32 connected to one of the handles 26. The stop surface 35 has a diameter greater than the diameter of the bore 34, such that the stop surface 35 can engage the periphery of the handle 26 around the bore 34 to maintain the rod 32 within the bore 34.

Adjacent the bore 34, the handle 26 having the bore 34 also includes a locking tab 36 pivotally connected to the end of the gripping handle 26 and including an aperture 38 therein through which the rod 32 extends. The rod 32 can slide through the aperture 38 formed within the tab 36 when the handles 26 are urged towards one another.

A spring 40 is disposed about the rod 32 between the locking tab 36 and the gripping handle 26 in which the bore 34 is formed. The spring 40 operates to urge the tab 36 away from the handle 26 to misalign the aperture 38 with the rod 32, thereby frictionally engaging the tab 36 with the rod 32 in order to retain the gripping handles 26 in a stationary position. The positioning of the spring 40 enables the handles 26 to be moved toward one another without resistance from the tab 36, as the movement of the handles 26 toward one another opposes the bias of the spring 40. However, when the handles 26 are released, the spring 40 pushes the tab 36 into the frictional engagement with the rod 32, effectively locking the handles 26 in the current position.

To disengage the locking mechanism 30, the tab 36 is moved towards the handle 26 to which it is secured against the bias of the spring 40 to disengage the tab 36 from the rod 32. This allows the handle 26 and tab 36, along with the spring 40, to slide along the rod 32 and move towards or away from the opposed gripping handle 26 to which the rod 32 is pivotally secured. With the locking mechanism 30, it is capable to engage the gripping handles 26 in a stationary position with regard to one another at any relative position by allowing the tab 36 to engage the rod 32 at an infinite number of locations along the rod 32.

Also, the design of the locking mechanism 30 does not have any sharp edges, teeth or ridges, as in prior art distractors and compressors, such that the mechanism 30 is less likely to become damaged even during regular usage, and is less likely to damage the gloves worn by an individual utilizing the tool 10. Preferably, the handle 26 to which the tab 36 is attached includes an inwardly extending flange 39 positioned generally parallel to the rod 32. The tab 36 is secured to the flange 39 adjacent the innermost end of the flange 39 to give the tab 36 a significant range of motion in either direction with respect to the rod 32. Also, the presence of the flange 39 functions as a guard to the tab 36, such that inadvertent contact with the flange 39 or rod 32 will not be able to disengage the tab 36 from the rod 32, maintaining the locked position of the handles 26.

Referring now to FIGS. 1-8, in order to mechanically translate the movement of the gripping handles 26 into corresponding compressive or distractive lateral movement of the tip members 12, a central shaft 42 is positioned within and extends through a central channel 44 defined in the central member 24. A first end 46 of the shaft 42 is positioned between and equidistant from each of the tip of members 12. The shaft 42 also includes a pair of sets of pivot members 48 each pivotally connected at one end to the first end 46 of the shaft 42 via pivot pins 50 and 52 engaged with the first end 46, and at the opposite ends to the tip members 12 via pivot pins 54-60, though other suitable connections (e.g., sliding connections) can be made between the pivot members 48 and the shaft 42 and tip members 12. In this configuration, as the shaft 42 slides through the channel 44 in the central member 24 in a direction towards the tip members 12, the shaft 42 operates to urge the tip members 12 always from one another in a distractive moment as a result of the engagement of the tip members 12 with the shaft 42 via the sets of pivot members 48. Conversely, as the shaft 42 slides through the channel in the central member 24 in a direction away from the tip members 12, the shaft 24 pulls the sets of pivot members 48 and the tip members 12 towards one another in a compressive movement.

Between the gripping handles 26, the central member 24 includes a guide sleeve 62 secured to the central member 24 around the channel 44 and through which the second end 64 of the shaft 42 extends. The sleeve 62 ensures that the shaft 42 moves in a strictly linear fashion with regard to the remainder of the tool 10.

Disposed on the second end 64 of the shaft 42 is an operational shifting member or saddle 66. The saddle 66 includes a central bore 68 through which the second end 64 of the shaft 42 extends. The saddle 66 is maintained in engagement with the shaft 42 by the sleeve 62 at one end, and by an end cap 70 secured to the second end 64 of the shaft 42 opposite the sleeve 62. Additionally, the saddle 66 is urged away from the central member 24 by a spring 69 disposed within the sleeve 62 and engaged at one end by a ring 69a secured to and extending outwardly from the saddle 66 partially into the sleeve 62, and by the central member 24 at the opposite end. The spring 69 functions to move the saddle 66 along the shaft 42 away from the central member 24 to move the tool 10 to the position shown in either FIGS. 1 and 2, or FIGS. 5 and 6 when the locking mechanism 30 is disengaged. The saddle 66 is also pivotally connected by pivot pins 71 or any other suitable connection, to one end of a pair of pivot arms 72 that are each pivotally connected at the opposite end to the gripping members 26 at a location spaced from the rod 32 by pivot pins 73.

The saddle 66 also includes a locking device 74 disposed within the body of the saddle 66 that at least partially obscures the central bore 68 extending through the saddle 66. The locking device 74 is selectively engageable with one of a number of notches 76 located in the second and 64 of the shaft 42 between the sleeve 62 and the end cap 70. These notches 76 are disposed on opposite sides of the center point 77 of the second end 64 of the shaft 42, such that the pivot arms 48 are either angled towards or away from the central member 24 when the saddle 66 and locking mechanism 74 engaged with these notches 76. When these saddle 66 is engaged with a notch 76 closer to the central member 24, as illustrated in the FIG. 1, the compression of the gripping handles 26 towards one another causes the shaft 24 to slide through the central number 24 towards the tip members 12, causing the tip members 12 to move outwardly in a corresponding distraction movement. Conversely, when the saddle 66 is engaged with notch 76 closer to the end cap 70, as shown in FIG. 2, the movement of the handle members 26 towards one another slides the central shaft 42 all way from the central number 24, drawing the tip members 12 towards one another in a compressive movement.

With the construction of the tool 10 according to the present invention, the amount of force required to move the handle members 26 towards one another is greatly lessened, such that the structural components of the tool 26 including the handle members 26 undergo less stress during operation of the tool 10. Consequently, the materials utilized in the construction of the tool 10 can be selected from materials that are more lightweight than prior art compression tools and distraction tools.

Additionally, as a result of the construction of the tool 10 with the central shaft 42 and the saddle 66, the stroke and leverage of the tool 10 can be altered by varying the position of the saddle 66 with regard to the shaft 42 in each mode of operation of the tool 10. This allows the power generated by the operation of the tool 10 to be varied by positioning the saddle 66 at the proper or desired location along the shaft 42. Further, the operation of the tool 10 in either mode is not strictly linear, such that less force is required to move the handles 26 near the end of the stoke of the tool 10.

Various other embodiments of the present invention are contemplated as being within the scope of the filed claims particularly pointing out and distinctly claiming the subject matter regarded as the invention.

I claim:

1. A combination compression/distraction tool comprising:
   a) a saddle including a channel formed therein;
   b) at least one tip member movably secured to one side of the saddle;
   c) a pair of handle members movably secured to the saddle opposite the at least one tip member; and
   d) a locking mechanism engaged between the pair of handle members, the locking mechanism including a locking shaft movably secured to one of the pair of handle members and a locking tab movably secured to the other handle member and engaged with the locking shaft wherein the locking shaft is slidably engaged within an aperture formed in the locking tab, further comprising a biasing member disposed between the locking tab and the handle member to which the locking tab is secured to bias the tab into engagement with the locking shaft.

2. The tool of claim 1 wherein the biasing member is disposed around a portion of the locking shaft extending between the locking tab and the handle member to which the locking tab is secured.

3. The tool of claim 1 wherein the locking shaft extends through an opening in the handle to which the locking tab is secured.

4. The tool of claim 1 wherein the locking shaft is frictionally engaged by the locking tab.

* * * * *